(12) United States Patent
Gal

(10) Patent No.: US 9,375,165 B2
(45) Date of Patent: Jun. 28, 2016

(54) SENSORS FOR INDUCTIVE PLETHYSMOGRAPHIC MONITORING APPLICATIONS AND APPAREL USING THE SAME

(71) Applicant: adidas AG, Herzogenaurach (DE)

(72) Inventor: Yoav Gal, Berkeley, CA (US)

(73) Assignee: adidas AG, Herzogenaurach (DE)

( * ) Notice: Subject to any disclaimer, the term of this patent is extended or adjusted under 35 U.S.C. 154(b) by 29 days.

(21) Appl. No.: 14/324,553

(22) Filed: Jul. 7, 2014

(65) Prior Publication Data

US 2014/0316295 A1 Oct. 23, 2014

Related U.S. Application Data

(60) Division of application No. 13/242,929, filed on Sep. 23, 2011, now Pat. No. 8,777,868, which is a continuation of application No. 11/233,317, filed on Sep. 21, 2005, now Pat. No. 8,034,001.

(60) Provisional application No. 60/699,698, filed on Jul. 15, 2005, provisional application No. 60/611,900, filed on Sep. 21, 2004.

(51) Int. Cl.
*A61B 5/08* (2006.01)
*A61B 5/113* (2006.01)
*A61B 5/00* (2006.01)
*A61B 5/091* (2006.01)

(52) U.S. Cl.
CPC .............. *A61B 5/0809* (2013.01); *A61B 5/091* (2013.01); *A61B 5/1135* (2013.01); *A61B 5/6804* (2013.01); *A61B 5/6831* (2013.01); *A61B 2562/02* (2013.01)

(58) Field of Classification Search
CPC .............................. A61B 5/091; A61B 5/0809
See application file for complete search history.

(56) References Cited

U.S. PATENT DOCUMENTS

| | | | |
|---|---|---|---|
| 4,016,868 A | 4/1977 | Allison | |
| 4,308,872 A | 1/1982 | Watson et al. | |
| 4,373,534 A | 2/1983 | Watson | |
| 4,433,693 A | 2/1984 | Hochstein | |

(Continued)

FOREIGN PATENT DOCUMENTS

WO WO 2005/115242 12/2005

OTHER PUBLICATIONS

Fahrenberg, "Origins and Development of Ambulatory Monitoring and Assessment", in Fahrenberg et al., 2001, Progress in Ambulatory Assessment Seattle, WA: Hogrefe and Huber.

*Primary Examiner* — Christian Jang

(74) *Attorney, Agent, or Firm* — Sterne, Kessler, Goldstein & Fox P.L.L.C.

(57) ABSTRACT

This invention includes improved IP sensors that both have improved sensitivity, performance, and other properties and are multifunctional. The improved IP sensors have IP sensor conductors with waveforms having legs that are substantially parallel throughout the operating range of stretch. The multifunctional IP sensors include, in addition to IP sensors, accessory conductors, additional sensors, and other compatible modules. This inventions also includes embodiments of apparel incorporating the improved IP sensors. This apparel can range from band-like to shirt-like, and so forth, and include one or more IP sensors sensitive to expansions and contractions of underlying regions of a monitored subject.

10 Claims, 9 Drawing Sheets

(56) References Cited

U.S. PATENT DOCUMENTS

| | | | |
|---|---|---|---|
| 4,452,252 | A | 6/1984 | Sackner |
| 4,456,015 | A | 6/1984 | Sackner |
| 4,648,407 | A | 3/1987 | Sackner |
| 4,753,088 | A | 6/1988 | Harrison et al. |
| 4,777,962 | A | 10/1988 | Watson et al. |
| 4,800,495 | A | 1/1989 | Smith |
| 4,807,640 | A | 2/1989 | Watson et al. |
| 4,815,473 | A | 3/1989 | Watson et al. |
| 4,817,625 | A | 4/1989 | Miles |
| 4,834,109 | A | 5/1989 | Watson |
| 4,860,766 | A | 8/1989 | Sackner |
| 4,960,118 | A | 10/1990 | Pennock |
| 4,966,155 | A | 10/1990 | Jackson |
| 4,986,277 | A | 1/1991 | Sackner |
| 5,007,427 | A | 4/1991 | Suzuki et al. |
| 5,040,540 | A | 8/1991 | Sackner |
| 5,074,129 | A | 12/1991 | Matthew |
| 5,131,399 | A | 7/1992 | Sciarra |
| 5,159,935 | A | 11/1992 | Sackner et al. |
| 5,178,151 | A | 1/1993 | Sackner |
| 5,301,678 | A | 4/1994 | Watson et al. |
| 5,331,968 | A | 7/1994 | Williams et al. |
| 5,348,008 | A | 9/1994 | Bornn et al. |
| 5,353,793 | A | 10/1994 | Bornn |
| 5,416,961 | A | 5/1995 | Vinay |
| 5,447,164 | A | 9/1995 | Shaya et al. |
| RE35,122 | E | 12/1995 | Coreman et al. |
| 5,533,511 | A | 7/1996 | Kaspari et al. |
| 5,544,661 | A | 8/1996 | Davies et al. |
| 5,564,429 | A | 10/1996 | Bornn et al. |
| 5,588,425 | A | 12/1996 | Sackner et al. |
| 5,820,567 | A | 10/1998 | Mackie |
| 5,899,855 | A | 5/1999 | Brown |
| 5,913,830 | A | 6/1999 | Miles |
| 5,991,922 | A | 11/1999 | Banks |
| 6,015,388 | A | 1/2000 | Sackner et al. |
| 6,047,203 | A | 4/2000 | Sackner et al. |
| 6,066,093 | A | 5/2000 | Kelly et al. |
| 6,067,462 | A | 5/2000 | Diab et al. |
| 6,142,953 | A | 11/2000 | Burton et al. |
| 6,223,072 | B1 | 4/2001 | Mika et al. |
| 6,254,551 | B1 | 7/2001 | Varis |
| 6,341,504 | B1 | 1/2002 | Istook |
| 6,413,225 | B1 | 7/2002 | Sackner et al. |
| 6,449,504 | B1 | 9/2002 | Conley et al. |
| 6,551,252 | B2 | 4/2003 | Sackner et al. |
| 6,604,115 | B1 | 8/2003 | Gary et al. |
| 6,633,772 | B2 | 10/2003 | Ford et al. |
| 6,721,594 | B2 | 4/2004 | Conley et al. |
| 6,727,197 | B1 | 4/2004 | Wilson et al. |
| 6,775,389 | B2 | 8/2004 | Harrison et al. |
| 6,783,498 | B2 | 8/2004 | Sackner et al. |
| 2002/0032386 | A1* | 3/2002 | Sackner et al. ............... 600/536 |
| 2003/0135127 | A1 | 7/2003 | Sackner et al. |
| 2004/0225227 | A1 | 11/2004 | Newman |
| 2005/0054941 | A1 | 3/2005 | Ting et al. |
| 2005/0119586 | A1 | 6/2005 | Coyle et al. |
| 2005/0228234 | A1 | 10/2005 | Yang |
| 2005/0240087 | A1 | 10/2005 | Keenan et al. |
| 2006/0036183 | A1 | 2/2006 | Sackner et al. |

\* cited by examiner

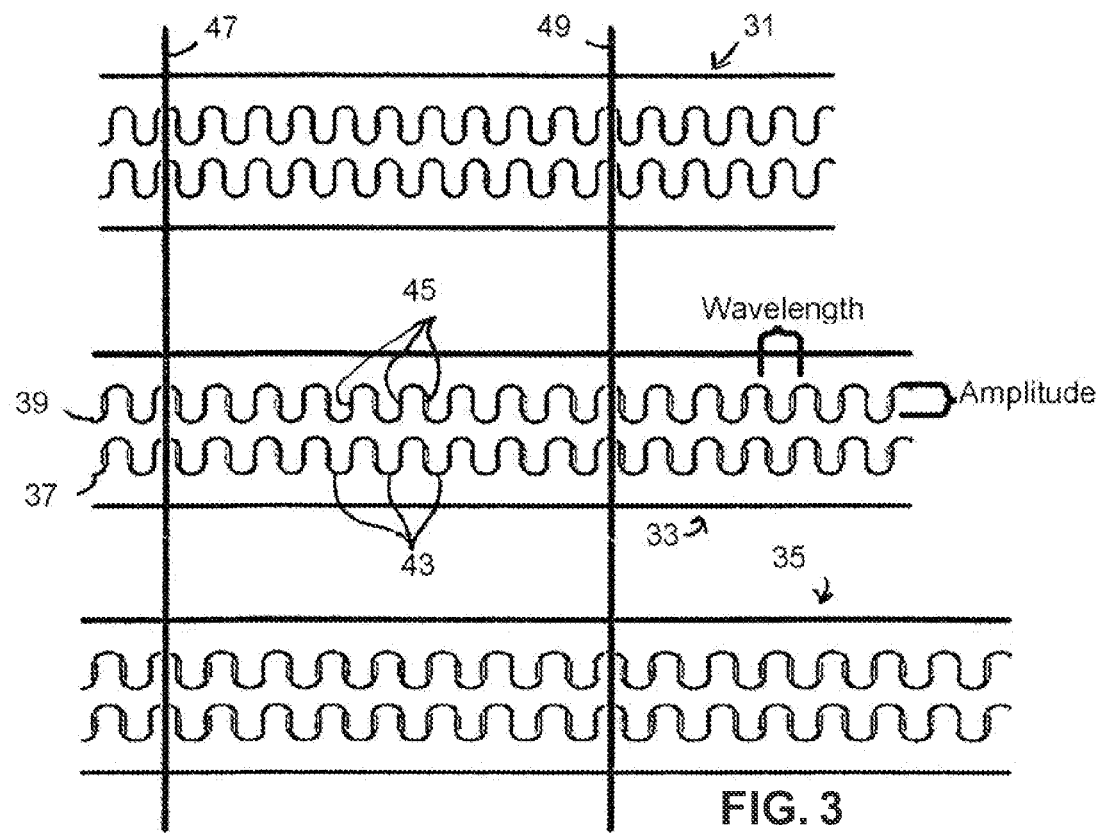
FIG. 3
FIG. 4A
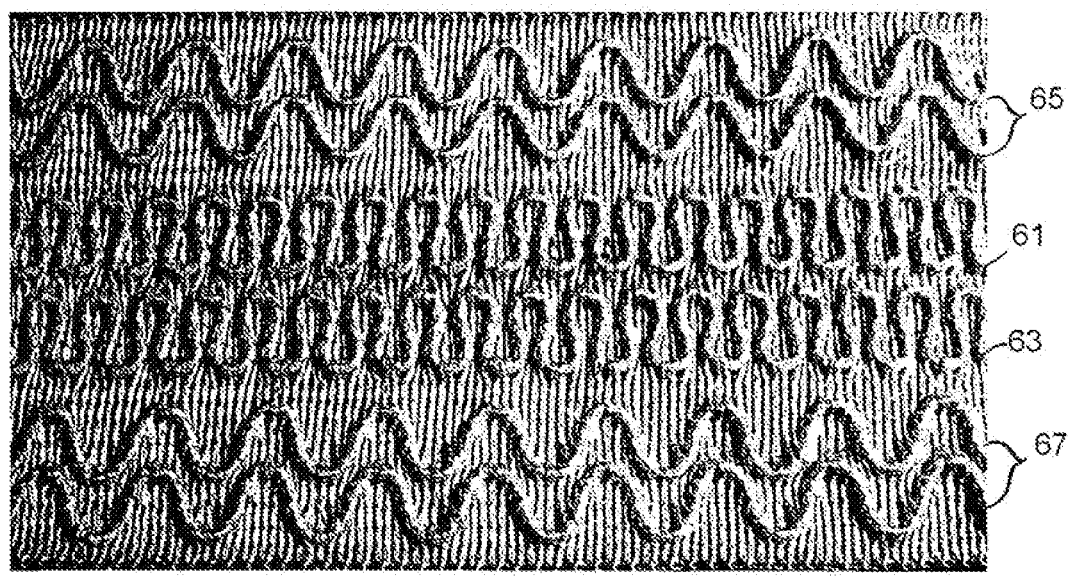

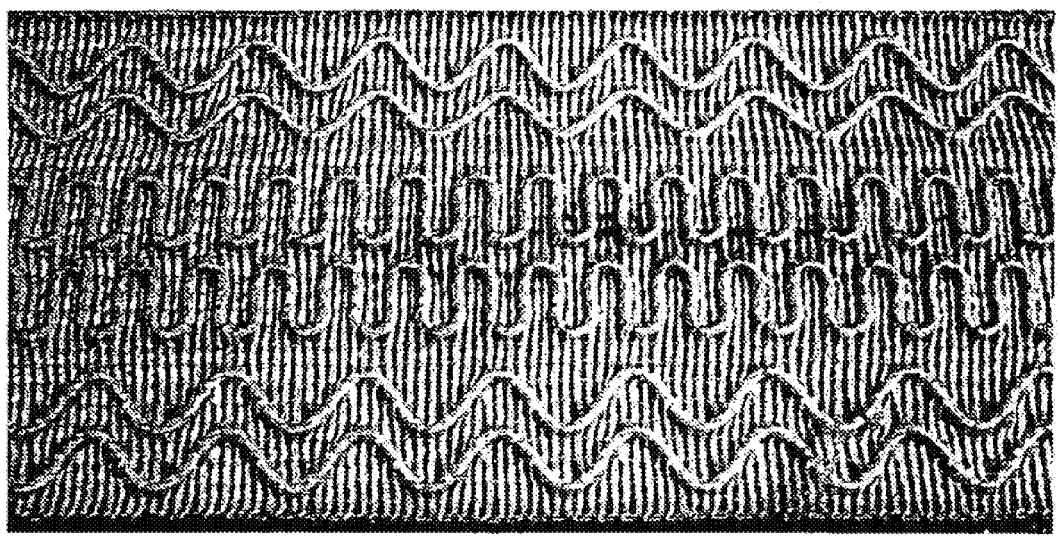
FIG. 4C
FIG. 4B
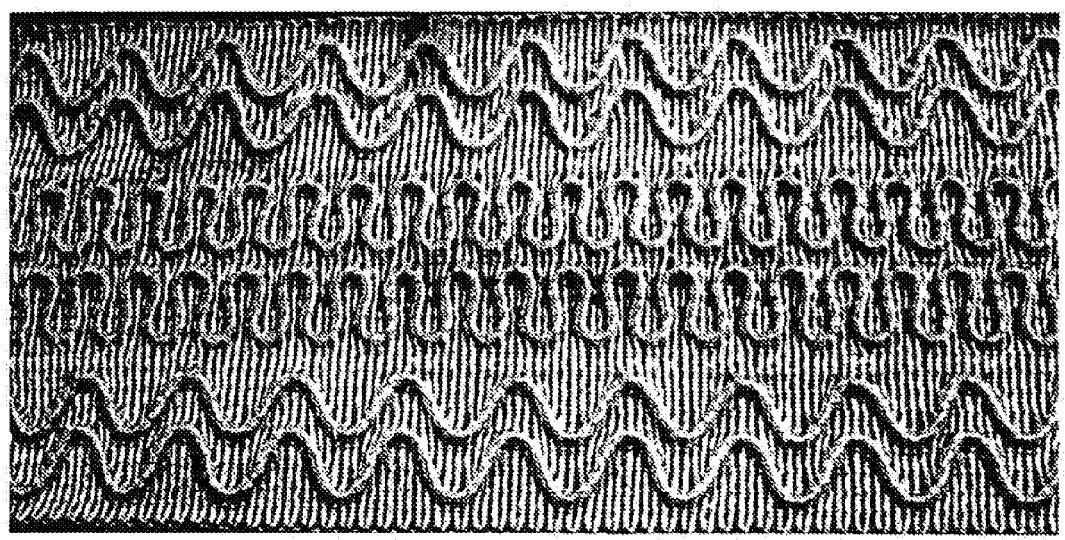

SENSORS FOR INDUCTIVE PLETHYSMOGRAPHIC MONITORING APPLICATIONS AND APPAREL USING THE SAME

This application is a divisional of U.S. application Ser. No. 13/242,929, filed on Sep. 23, 2011, now U.S. Pat. No. 8,777, 868, which is a continuation of U.S. application Ser. No. 11/233,317, filed on Sep. 21, 2005, now U.S. Pat. No. 8,024, 001, which claims the benefit of U.S. provisional application No. 60/611,900, now expired, filed Sep. 21, 2004, and of U.S. provisional application No. 60/699,698, now expired, filed Jul. 15, 2005; each of these applications are incorporated by reference in their entireties herein for all purposes.

FIELD OF THE INVENTION

The present invention provides improved sensors for inductive plethysmographic ("IP") monitoring applications and embodiments of apparel incorporating the improved sensors; in particular the improved sensors have improved performance and multifunctional capabilities.

BACKGROUND OF THE INVENTION

Inductive plethysmography (IP) is a measurement technology useful for physiological monitoring, especially for ambulatory physiological monitoring. IP sensors can be disposed on monitored subjects, either directly or attached to or incorporated into various kinds of comfortable, unobtrusive garments, for example, in bands, or in partial-shirts, or in shirts, or on partial body suits, or in full body suits, or in caps, and the like. See, e.g., U.S. Pat. No. 6,551,252 B2 issued Apr. 22, 2003. Often, respiration is monitored by combining signals from an IP sensor about the rib cage (RC) and an IP sensor about the abdomen (AB). Coefficients used for combining RC and AB signals in respiration signals can be determined by calibration procedures. See, e.g., U.S. Pat. No. 4,834,109 issued May 30, 1989 and U.S. Pat. No. 6,413,225 B1 issued Jul. 2, 2002. It is also known that differential lung function can be obtained by combining signals from more localized IP sensors overlying the right and left lungs. See, e.g., U.S. Pat. No. 5,159,935 issued Nov. 3, 1992. All four of these cited patent are incorporated herein by reference in their entireties for all purposes.

Further, signals from one or more IP-based sensors about a subject's thorax and/or abdomen can be processed and interpreted to provide, for example, respiratory rates, respiratory volumes, and indications of respiratory events such as coughs and the like. See, e.g., U.S. patent application Ser. No. 10/822, 260 filed Apr. 9, 2004 (which is incorporated herein by reference in its entirety for all purposes). Signals from one or more IP-based sensors about a subject's thorax at the level of the xiphoid process can be processed and interpreted to provide, for example, cardiac stroke volumes, and the like. See, e.g., U.S. Pat. No. 6,783,498 B2 issued Aug. 31, 2004 (which is incorporated herein by reference in its entirety for all purposes).

Generally, an IP sensor includes a conductive element that is placed about, usually enclosing, a portion of the body to be monitored. As the size of the enclosed body portion changes, for example, because of respirations and/or cardiac contractions, electrical properties of the conductive element changes. Sensor electronics measures these change and produces output signals, which can be processed into data reflective of areas, circumferences, diameters, and similar geometric measures, of the monitored body part enclosed body cross section. The resulting area, circumference, diameter, and similar information is useful for physiological monitoring applications.

Since it is important that the conductive element, usually a wire, move with the monitored body part, this element is usually not directly mounted but it supported by an elastic material which is in contact with the monitored body part. The supporting elastic material has usually been a knitted, woven, crocheted, or braided textile on which the sensor wire is mounted and affixed in a wavy, sinuous, or approximately sinusoidal pattern. See, e.g., U.S. Pat. No. 6,341,504 B1 issued Jan. 29, 2002 (which is incorporated herein by reference in its entirety for all purposes).

However, these known IP sensors have generally been limited to performing only IP sensor functions. Furthermore, their sensor functions has lacked desirable sensitivity, performance, and other important sensor properties.

Citation or identification of any reference in this section or any section of this application shall not be construed that such reference is available as prior art to the present invention.

SUMMARY OF THE INVENTION

Therefore, objects of this invention include providing improved IP sensors that are both multifunctional and have improved sensitivity, performance, and other properties. Objects of this invention also include embodiments of apparel incorporating the improved sensors.

This improved sensor includes a supporting elastic material that is intended to be arranged on a body part of the monitored subject. When so arranged, the material is stretchable through an operating range of stretch by expansion and contraction of the underlying body part. The material includes one or more sensor conductors operably affixed to the elastic material in a pattern of repeated unit waves that stretch and contract with the supporting elastic material. Each of these waves is configured to have leg portions that are substantially parallel and remain substantially parallel throughout the operating range of stretch. Preferably, the leg portions deviate no more than approximately ±2° or less from parallelism throughout the operating range of stretch.

The unit waves of the sensor conductor preferably have a spatial frequency greater than approximately 5 per in., and more preferably approximately 6 per in., when the supporting elastic is stretched at less that the operating range of stretch. The conductors are preferably of a fine a wire as is consistent with DC resistance requirements, and is usually of 27 AWG or higher. As the sensor conductors stretch and contract throughout the operating range of stretch, an electrical characteristic of the sensor conductor changes, preferably linearly with the stretch of the supporting. The electrical characteristic is usually an AC impedance which preferably is substantially, The sensor conductors can have various orientations with respect to the supporting elastic. For example, their leg portions can extend substantially perpendicularly to the surfaces of the supporting elastic, or their leg portions can be substantially parallel and remain substantially parallel throughout the operating range of stretch, or their leg portions can be angled to extend perpendicular between the surfaces of supporting elastic and parallel along the surfaces of the supporting elastic.

The sensor of this invention are can include one or more accessory conductors affixed to the elastic material. Their pattern also comprises repeated unit waves that stretch and contract with the supporting elastic material, but the unit waves of the accessory conductor and the unit waves of the sensor conductor usually have different spatial frequencies and preferably have a smooth pattern without substantially parallel leg portions. In particular, the accessory conductor have a spatial frequency preferably less than approximately 3 per in. The accessory conductors can include comprises micro-coax. A sensor often has two or more sensor conductors and four of more accessory conductors and up to ten or more total conductors.

When applied to inductive plethysmography (IP), the sensor conductors are bridged and are operably linked to conductors external to the supporting elastic. Thus, when seen from the external conductors, two sensor conductors are electrically continuous. This configuration allow advantageous arrangements on monitoring garments where the sensor conductors need not be interrupted by garment, lines of closure and limits external connections to a single location on the sensor conductors.

These sensor can include one or more additional sensors affixed to the supporting elastic, such as microphones, body-temperature thermometers, ECG electrodes, accelerometers, sensors for electroencephalogram signals, sensors for electrooculogram signals, sensors for electromyogram signals, and the like. Such additional sensors are advantageously operably linked externally by an accessory conductor which conveys signal from the sensor.

The elastic material can be woven, and/or knitted, and/or crocheted, and/or braided material, and/or extruded material, of the like. Generally, the materials are made by conventional means and machines known in the art but adapted to distribute conductors across the materials surface.

This invention also includes methods of physiologically monitoring a subject that employ the improves sensors of this invention. These methods include arranging an improved sensor on a body part of the monitored subject, and measuring an electrical characteristic of the sensor conductor which changes as the supporting elastic is stretched throughout the operating range of stretch and from which conductor length can be determined. The electrical characteristic is usually measured across external leads operably linked to the sensor conductors. The measured characteristic is AC impedance that is usually substantially inductive in nature and that varies with substantially no hysteresis throughout the operating range of stretch. The variation with stretch is preferably as rapid as possible, and more preferably linear throughout a substantial fraction of the operating range.

In preferred embodiments, these characteristics are measured by applying an excitation signal to the sensor conductor that possess a frequency determined at least in part by the sensor conductor. The frequency of the excitation signal is then measured.

This invention also includes physiological monitoring apparel that include the improved IP sensors of this invention. The apparel includes a worn by a subject that supports the supporting elastic material and the IP sensor. The garment can be band-like, or shirt-like, or be otherwise configures Different physiological information can be obtained by careful placement on sensors on the garment. For example, by arranging one sensor conductor arranged on a left lateral part of the rib cage of the subject and another sensor conductor on a right lateral part of the rib cage of the subject, differential lung function can be determined by comparing difference between the two rib-cage measurements. Also, total lung function can be determined by cumulating both the measurements. Measurement quality can be improved by includes one sensor conductor arranged on a left lateral part of the abdomen of the subject and another conductor on a right lateral part of the abdomen of the subject, and by combining these abdominal signals with the rib cage signals.

These garments can include additional sensors either attached to the IP sensor supporting elastic or otherwise carried by the garment. Additional sensors can include microphones, body-temperature thermometers, ECG electrodes, accelerometers, sensors for electroencephalogram signals, sensors for electrooculogram signals, sensors for electromyogram signals, and the like. The IP sensor used here and the garments can also have one or more accessory conductors that often link the additional sensor to processing circuitry. The garment fabric, as well as the supporting elastic, material, can be woven, and/or knitted, and/or crocheted, and/or braided, and/or extruded material, and so forth.

In a preferred embodiment, the invention includes a physiological sensor for a monitoring a subject that comprises a supporting elastic material adapted to be arranged on a body part of the monitored subject and, when so arranged, stretchable through an operating range of stretch by expansion and contraction of the underlying body part; at least one sensor conductor operably affixed to the elastic material in a pattern comprising repeated unit waves that stretch and contract with the supporting elastic material wherein each unit wave is configured to have leg portions that are substantially parallel and that remain substantially parallel throughout the operating range of stretch.

Aspect of this preferred embodiment include: that the leg portions deviate approximately $\pm 2°$ or less from parallelism throughout the operating range of stretch; that, when the sensor is not stretched, the leg portions converge together from crest of a unit wave to the base of the unit wave; that the unit waves of the sensor conductor have a spatial frequency greater than approximately 5 per in. when the supporting elastic is stretched at less than the, operating range of stretch; that the unit waves of the sensor conductor have a spatial frequency greater than approximately 6 per in. when the supporting elastic is stretched at less than the operating range of stretch; and that sensor conductor comprises wire of 27 AWG (America Wire Gauge) or higher.

Further aspect of this preferred embodiment include: that an electrical characteristic of the sensor conductor changes as the supporting elastic is stretched throughout the operating range of stretch; that the electrical characteristic is substantially free of hysteresis over a plurality of cycles of stretching and relaxation; that the plurality of cycles of stretching and relaxation comprises a period of monitoring the subject; that the period of monitoring the subject is less than one hour, or less than twelve hours, or less than twenty-four hours; that the electrical characteristic comprises an AC impedance of the sensor conductor; the impedance is substantially an inductive impedance; and that the electrical characteristic depends substantially linearly on the stretch in a substantial portion of the operating range of stretch.

Further aspect of this preferred, embodiment include: that the IP conductor is affixed to the supporting elastic so that when the IP sensor is arranged on the body part, the electrical characteristic is substantially free of hysteresis over a plurality of cycles of stretching and relaxation; that at least one accessory conductor affixed to the elastic material in a pattern comprising repeated unit waves that stretch and contract with the supporting, elastic material, wherein the unit waves of the accessory conductor have a spatial frequency less than the spatial frequency of the unit waves of the sensor conductor; that the unit waves of the accessory conductor have a spatial frequency less than approximately 3 per in; that the unit waves have a smooth pattern without substantially parallel leg portions; that the accessory conductor comprises micro-coax; that the sensor conductors are positioned between the accessory conductors.

It should be understood that sensor of the preferred embodiment is included in additional embodiments of the physiological sensors of this invention and of the apparel of this invention. Similarly, the aspects of this preferred embodiment can be included the above additional embodiments. Further aspects and details and alternate combinations of the elements of this invention will be apparent from the following detailed description and are also within the scope of the inventor's invention.

BRIEF DESCRIPTION OF THE DRAWINGS

The present invention may be understood more fully by reference to the following detailed description of the preferred embodiment of the present invention, illustrative examples of specific embodiments of the invention and the appended figures in which:

FIG. 3 illustrates an embodiment of the preferred patterns of IP sensor conductors;

FIG. 4A-C illustrate an implementation of the preferred patterns of IP sensor conductors;

DETAILED DESCRIPTION OF THE PREFERRED EMBODIMENTS

Following a summary of IP technology, described herein are preferred embodiments of the improved inductive plethysmographic ("IP") sensors configurations of this invention; then multifunctional and otherwise, improved IP sensors; and finally, novel, and/or exemplary applications of these IP sensors and elastic materials in physiological monitoring. In the following (and in the application as a whole), headings and legends are used for clarity and convenience only.

Inductive plethysmography (IP) provides signals reflecting the varying sizes of a body part, specifically the volume of the body part. An elastic IP sensor that include a conductive element is arranged on a body part in a manner so that the conductive element expands and contracts along with the underlying part. Since the electrical properties, often the inductance, of the conductive element vary with its physical configuration, measurements of the element characteristics will reliably reflect size of the body part. Specifically, the electrical properties vary with the length of the sensor, so that, when a sensor is arranged to substantially enclose a body part, a plethysmographic volume can be derived from the sensor output. In most cases, instead of directly attaching an IP sensor conductor to the measured body part, the sensor conductor is operably affixed or operably mounted on an elastic material, e.g., a woven, knitted, braided, or the like, band, and this elastic material can then be arranged on the body part, e.g., by being part of a garment.

As used herein, an "IP sensor" is such a combination of a sensor conductor (or sensor "conductive element"), the "sensor conductor", and supporting elastic material, the "supporting elastic". The IP sensor is linked to "IP electronics", which measures varying electrical characteristics of the sensor conductor and preferably provides a digitized output signal. "Operably affixed" or "operably mounted" is used herein to mean that the conductive element is affixed to the supporting elastic so that it will change proportionally as the supporting elastic stretches and contracts. The sensor conductor may be operably affixed by, e.g., incorporation into the elastic. Although throughout the following description the sensor conductor is described as a wire of particular characteristics, this is not limiting. In other embodiments, the sensor conductor can be, e.g., formed from a metallic or non-metallic conductive thread or filament. Also, although throughout the following description the supporting elastic is usually a woven, knitted, braided, or the like, band, this also is not limiting. Supporting elastic can be manufactured by other techniques. Additionally, a sensor conductor may be affixed directly to a partially or entirely elastic garment which then serves as the supporting elastic.

Figure 1:
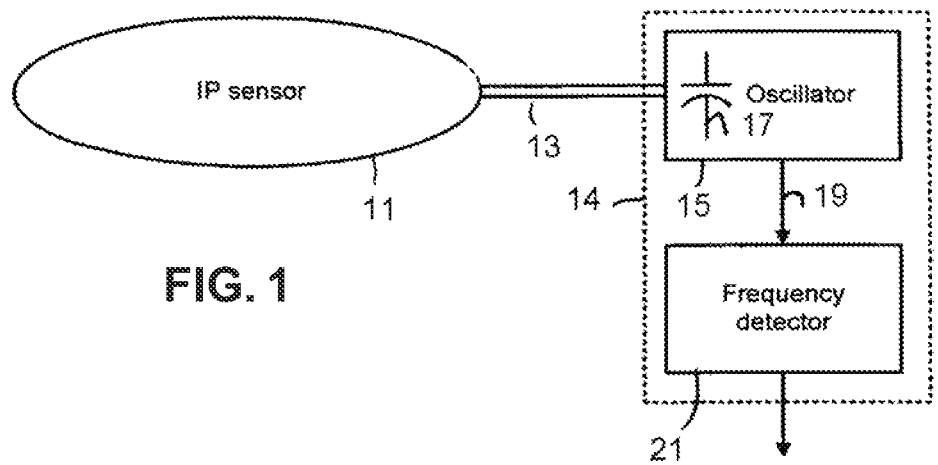
FIG. 1 illustrates an embodiment of processing of IP sensor signals.

IP sensor electronics can measure an electrical characteristic of the sensor conductor by the various means known in the arts that are appropriate, e.g., by being suitably miniaturizeable and portable, to a particular embodiment of this invention. In the preferred IP sensor to be described, the impedance is primarily inductive and a preferred measurement technique indirectly measures inductance by applying an excitation signal to the sensor element and using the natural resonance frequency as dictated by the impedance of the sensing element to infer an output value that is linear in relation to the sensor's elongation. This measurement technique, illustrated by FIG. 1, incorporates the sensor conductor into an oscillator circuit in a manner so that the oscillator frequency will vary with inductance of the sensor conductor. Oscillator frequency is then detected, digitized, and output using one of the known, reliable and accurate frequency detection techniques.

This measurement As illustrated, sensor conductor 11 is connected by link 13 to impedance measuring circuit 14, impedance being determined by inductance at the frequency of the excitation signal. Sensor conductor 11 may be in the form of a circumferentially-continuous loop. More preferably as subsequently described, the sensor conductor is arranged so that it is not circumferentially continuous, but instead is interrupted in a limited region 12. In preferred embodiments, impedance measuring circuit includes oscillator 15, which is configured to match the response characteristics of the oscillator circuit with those of the sensor conductor across the operating frequency range of the oscillator. The sensor conductor in cooperation with other elements of the oscillator tuning circuit 17 determines the frequency of oscillator output signal 19. Finally, frequency detector 21 detects oscillator frequency by known techniques, such as, e.g., by counting signal cycles during a reference time interval; or by phase locking oscillator 15 to a stable reference frequency (not illustrated); or the like.

Preferred Arrangement of IP Sensor Conductors

The inventors have discovered preferable IP sensors with considerably improved performance the remain within practical constraints such as manufacturability, cost, and the like. The following describes preferred design, principles leading to the improved sensors of this invention discovered and applied by the inventors. The following also describes the designs of particular improved sensors that are preferred for embodiments of this invention directed to measuring chest and abdomen sizes and that can be readily manufactured and activated by miniature and portable sensor electronics. It should be understood that these particular preferred sensors are not limiting, because they represent one balance sensor of performance against other important sensor characteristics for a few current measurement tasks.

Other balances lead to different preferred embodiments. And in view of following description, it will be readily apparent to one of skill in the art how to make improved sensors that represent different balances of performance against other characteristics and/or that are suitable for other measurement tasks. For example, sensor performance can be improved even further in embodiments where manufacturability is less important. Also, sensors can be developed for measurement of body parts of animals of all sizes. Indeed, animal physiological monitoring, veterinary medicine, or the like, are expected and intended applications of this invention. Furthermore, it will also be readily apparent how to adapt current improved sensors to future technologies for conductive elements, elastic materials, and garments.

Figure 2:
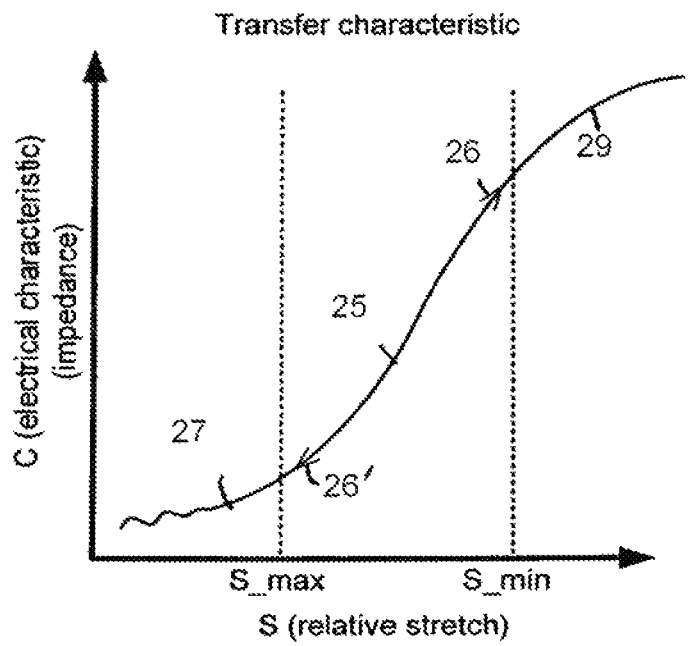
FIG. 2 illustrate preferred IP sensor performance.

With this in mind, FIG. 2 illustrates a transfer characteristic of a preferred IP sensor of the invention. The horizontal axis illustrates the relative linear elongation, or stretch, of a sensor. Relative stretch is a measure of the ratio of a baseline dimension of an IP sensor to the same dimension when the IP sensor is stretched by, e.g., expansions and contractions of an underlying body part such as a chest of a measured subject. It is a preferred stretch measure because it applies equally to IP sensor of a wide range of dimensions. During normal operation, relative stretch generally varies between the illustrated bounds, S_min and S_max, where S_min is the stretch when the body part being, measured is most contracted while S_max the stretch when the body part is more expanded. Overall, relative stretch compared to minimum sensor dimension is preferably 100% or more. For typical physiological measurements, the operating, range of relative stretch is from 0.1% or less up to 10-15% or less for most physiological process. Additionally, IP sensors should be at least comfortable and unobtrusive to a monitored subject for stretch throughout the operational range of relative stretch. The modulus of the sensor elastic should be large so that the sensor conductor has little or no motion with respect to the measured body part during use, yet not so large as to require a stretching force that is obtrusive or uncomfortable to a wearer.

In response to varying stretch, an electrical characteristic of the sensor conductor, usually its AC impedance, also varies in a manner generally illustrated by the graphed response line in FIG. 2. The vertical axis in FIG. 2 illustrates possible values of the sensor's electrical characteristic, usually impedance. The response (or transfer) characteristic illustrated by an exemplary sigmoidal curve that is usually realized by actual sensors. This exemplary curve is not limiting; other transfer characteristics are possible and have been found. More preferred IP sensor conductors are arranged to have a substantially linear transfer characteristic throughout as much of the operating range as possible. Most preferred sensor, have a linear characteristic throughout the entire operating range. Deviations from linearity of more than ±10% are generally substantial; preferably deviations are no more than ±1%, or even more preferably no more than ±0.1%.

The response characteristic of sensor of this invention has important preferred properties. A first important property is that the characteristic lacks significant hysteresis. More explicitly, as the sensor stretches 26 and relaxes 26' the value of the electrical characteristic when the sensor is at a particular level of stretch is substantially identical to values when the sensor was previously at that particular level of stretch and will be identical when the sensor will be at that particular level of stretch. In other words, the transfer characteristic is as illustrated by line 25; the sensor's electrical characteristic is uniquely and precisely defined at each level of stretch in the operational range of stretch. The accuracy by which stretch can be inferred from a current electrical characteristic is limited by variability due to hysteresis. If an accuracy of 1% or better, or 0.1% or better, or similar, hysteresis must be substantially absent to the extent that variability due to hysteresis is less than 1% or better, or less than 0.1% or better, respectively, and so forth.

Practically, hysteresis is preferably substantially absent within at least one measurement session. The transfer characteristic preferably does not drift overall between measurement sessions. If such drift occurs, interpretation of sensor output is preferably adjusted accordingly. Preferred sensor have no or limited drift over a lifetime of 10, or 20, or 30, or more million cycles of stretching and relaxation.

Another important characteristic of the sensor conductor configuration is that the slope of the transfer characteristic in the operating range of relative stretch be as great as possible. With larger the slopes, relative stretch can be inferred from measured electrical characteristic with more accuracy. Consequently, the largest slopes within other constraints are preferred.

Given a preferred IP sensor with substantially no hysteresis (to the desired level of accuracy) and as great a slope as possible, the preferred operating range can be selected as follows. When the sensor is substantially free of stretch 27 the sensor conductor is generally more limp and free to move with respect to the elastic or to not stretch with the elastic. In these stretch ranges, the transfer characteristic becomes flatter and more non-linear, even unpredictable, S_min should be set above region 27. When the sensor approaches a physical limit of stretch 29, the sensor conductor is unable to respond equally to further increases of stretch and the transfer characteristic becomes flatter again. S_max should be set below this region. In FIG. 2, the preferred region of operation relative stretch is 25.

The electrical characteristic of the preferred IP sensors is AC impedance. Further, the impedance of the preferred sensor at an operating frequency range is predominantly inductive. Response slope is improved as the inductive component of the impedance increases. Resistance and capacitance of the sensor conductor should be minimized, and in preferred sensors R is approximately 0.5Ω and C is approximately 30 pF. As seen by the electronics, the linking wires to the sensor elements (13 in FIG. 1) are an electrical part of said element and preferably contribute a negligible amount of impedance variation when subjected to positional changes. Practical preferred values for sensor of the length required in adult subjects are less than 1Ω resistance and 60 to 100 pF capacitance. The DC resistance of the sensor conductive element should be kept to a minimum (preferably, approximately 1Ω or less).

The particular preferred sensors as implemented in this application operate in a frequency range from approximately 150 kHz to approximately 600 kHz, and preferably in a frequency range from approximately 300 kHz to approximately 310 kHz. In more physiological application, the relative frequency change across the operational range of stretch will be small so the associated electronics preferably accurately measures frequency, e.g., accuracy of 1 part in at least 8000. Hysteresis should be absent to A similar level.

It should be noted that since the frequency itself is linear with 1/SQRT(L), designing to have a strictly linear L would result in a non-linear frequency response. More generally, instead of specific L values, it is preferred to be able to infer from the sensor electrical characteristic a value that is linear in relation to stretch. In fact, Thus, response characteristic 25 in FIG. 2 should be as steep as possible while maintaining the largest possible linear zone when the sensor element varies from unstretched to beyond the upper limit of the range of operational stretch. The linear portion is expected to be seen someplace in the middle of these two mechanical limits.

Otherwise stated, the preferred IP sensors are a form of length sensor, responding to relative changes in their length. Further, they function as length sensors in a wide range of sizes and three-dimensional configurations, even if formed into a three dimensional shape. It is believed that this is because their inductance is due primarily to local magnetic fields of nearby unit waves (see below) and only little affected to magnetic fields of distant portions of the sensor.

It has been found that the preferred IP sensors described below as well as sensors constructed according to design guidelines in this application have the above preferred characteristics. The preferred sensors to be described have a range of relative stretch in which a hysteresis free transfer characteristic is found, and moreover in a majority of instances, have a substantial linear region within that range of stretch. Given a preferred sensor, therefore, a lower bound and an upper bound on the relative stretch can be found within which the sensor satisfies the preferred sensor characteristics. An operational range of relative of relative stretch, that is an S_min and an S_max, can then be selected within this range. In many case, the operational range can be selected so have a substantial linear region. A linear region is considered substantial if it, is at least or greater than one half of the operational range of relative stretch.

The preferred transfer characteristic described are achieved with the preferred arrangements of the sensor conductors on the supporting elastic. A sensor conductor is operably affixed as a waveform of comprising repeating substantially similar unit waves. FIG. 3 schematically illustrates an IP sensor, e.g., sensor 33 having two sensor wires 37 and 39 mounted on supporting elastic 41 in such a preferred pattern. Indicated also are conventional unit wave parameters amplitude (A) and wavelength ($\Lambda$) (wavelength is the inverse of frequency (F), or $\Lambda=1/F$) It is preferable that the manufacturing variation on both A and F be as small as manufacturing constraints permit, and in any case less than approximately 10%, variations of approximately 20% or more are to be avoided.

For IP sensor wires, the frequency parameter, F, should be as large, again, as manufacturing constraints allow, but not so large that the affixed conductor limits elasticity to the point of causing problems for a wearer For example, for woven, crocheted, and the like elastic, F cannot exceed spatial frequency of the elastic's fibers or threads. Further, with increased F, the supporting elastic carries more conductor which can impede stretchability and even become sensible or obtrusive to a wearer, even it F is not large enough to interfere with sensor elasticity. In the case of supporting elastic that is woven, crocheted, knitted, or the like, an F of approximately 5.0/in. (inch) or greater is preferable; an F of approximately 5.5/in. or greater is more preferable. Where the supporting elastic, its manufacture, and the weight of the conductor permits, F's of approximately 6.0/in. or greater are more preferably. Generally, the amplitude, A, should also be as large as possible, limited by available space on the supporting elastic and also by manufacturing constraints and wearer comfort. A is usually less than or approximately 1-2 in. In most preferred embodiments, an A of approximately 0.5 in or greater has been found satisfactory.

As will be discussed, it is often advantageous to have, instead of one sensor wire of amplitude A, two linked sensor wires in the space where the one wire would have been and with amplitude of approximately A/2. Sensor performance of two linked wires with amplitudes A/2 has been found to be approximately that of one sensor wire of amplitude A other things being equal. FIG. 3 illustrates such an arrangement of two parallel sensor wires in a space on the supporting elastic. Two linked sensor wires each with an A of 0.3 in to 0.5 in or greater has been found satisfactory. These parameters can be combined as an amplitude-wavelength ratio (or equivalently, a amplitude-frequency product). A value of this product of approximately 1.5 of greater is preferred, a value of 2 or greater is more preferred. Using an even numbered sensor conductors wires is also advantageous because then the terminus (external contacts) points of the conductors can be located close to each other. This permits operating the sensor element in any closed open or overlapping physical configuration without problems of interruption or external connection. Such a configuration also aids in attaining preferred properties for the linking wires (13 in FIG. 1).

Further, the shape of the unit waves has been discovered to be an important design feature. Generally, preferred unit waves have rising and falling portions (referred to herein as the "legs" of the unit waves) that are on-average substantially parallel throughout the operating range of stretch (from S_min to S_max). "Wavy", or "sinuous", or "sinusoidal", or the like, patterns that non-parallel or inclined legs are less advantageous and are not part of this invention. Preferred unit waves can have on-average substantially parallel throughout the operating range of stretch, these shapes differ primarily in how pairs of adjacent legs are bridged. Bridges (also, referred to herein as "caps") can vary between more square-like and linear present in more "square-like" unit waves and more rounded and smoothly varying present in more "U-like" unit waves, with more square-like unit waves being somewhat preferred to more U-like waves. Preferred unit waves have amplitude-wavelength ratios of approximately 2 or greater, with greater ratios being more preferred.

FIG. 3 illustrates an illustrated particular preferred sensor pattern having more U-like unit waves at three degrees of stretch. The illustrated unit waves have substantially parallel legs 45, and adjacent legs are bridged with more rounded caps 43. Importantly, the legs remain substantially parallel over an operating stretch range, from a stretch below the operating range 31, to an average operating stretch 33, and to an increased stretch above the operating range 35. Further, across the operating range, the wave pattern responds substantially linearly to stretch. For example, at lesser stretch 31, the indicated distance markers 47 and 49 mark the length of ten unit waves; at average operating stretch, 33, the same markers mark nine unit waves; and at greater stretch, 33, the same markers mark only eight unit waves. Although the unit waves illustrated in FIG. 3 are preferred and entirely adequate for the present invention, more square-like unit waves would be somewhat more preferred. The substantially parallel portion of the legs should extend over at least half of the unit-wave amplitude, and preferably over two-thirds or more of the, amplitude.

Furthermore, it is apparent that, in the sensor pattern of FIG. 3, legs of the unit waves remain virtually parallel throughout the operating range of stretch. In the absence of constraints, such sensor patterns are realizable with precise manufacturing methods. However, because of manufacturing constrains, cost constraints, and other constraining factors, actual implementations of preferred sensors of this invention often have unit waves with legs that, while remaining substantially parallel throughout the operating range of stretch, do not remain as parallel as in FIG. 3. Somewhat constrained implementations with sensor patterns having substantially parallel legs throughout the operating range of stretch are also within the scope of this invention.

It can be appreciated from subsequent FIGS. 4A-C and FIGS. 5A-B that the substantially-parallel leg portions of the unit wave comprise a substantially fraction of the amplitude of the unit wave. Preferably, the leg potions comprise at 0.3 or more of the amplitude, preferably 0.5 or more of the amplitude, and more preferably 0.7 or more of the amplitude.

FIGS. 4A-C illustrate an actual implementation of a preferred IP sensor of this invention at three degrees of stretch. Wires 61 and 63 are IP sensor conductors, and have a preferred pattern including U-like unit waves with substantially parallel legs at an F of approximately 6/in. Accessory conductors 65a, 65b, 67a and 67b are not IP sensor conductors, and have a sinusoidal pattern, which is not a part of the IP sensor conductor patterns of this invention, at an F of approximately 4/in. They are subsequently described. The supporting elastic is a crocheted band with elastic warp filaments and on-elastic weft filaments, and the conductors were attached to this elastic band during crocheting. Accordingly, this implementation was constrained by the capabilities of readily available crocheting machines.

In FIG. 4A, the IP sensor is substantially not stretched. FIG. 4B is at the lower end of the normal operating range of stretch, and FIG. 4A is at the upper end of the normal operating range. Examination of FIGS. 4B and 4C reveals that across the normal operating range of stretch the legs of the U-shaped unit waves remain substantially parallel. Equivalently stated, the distances between the legs is substantially constant from near the crest to near the base of the unit wave. Examination of FIG. 4A reveals that even in a substantially unstretched state, the legs of the unit waves remain substantially parallel. Further, these figures illustrate the considerably difference in behavior between the IP conductors and the accessory conductors during stretch. Examining conductors 65a, 65b, 67a and 67b in FIG. 4A as compared to FIG. 4B and as compared to FIG. 4C reveals that the legs of their sinusoidal unit waves diverge considerably during stretch, or equivalently, the distance between the legs near the base of the unit wave increases by a considerably greater amount that the distance near the unit wave's crest.

Figure 5A:
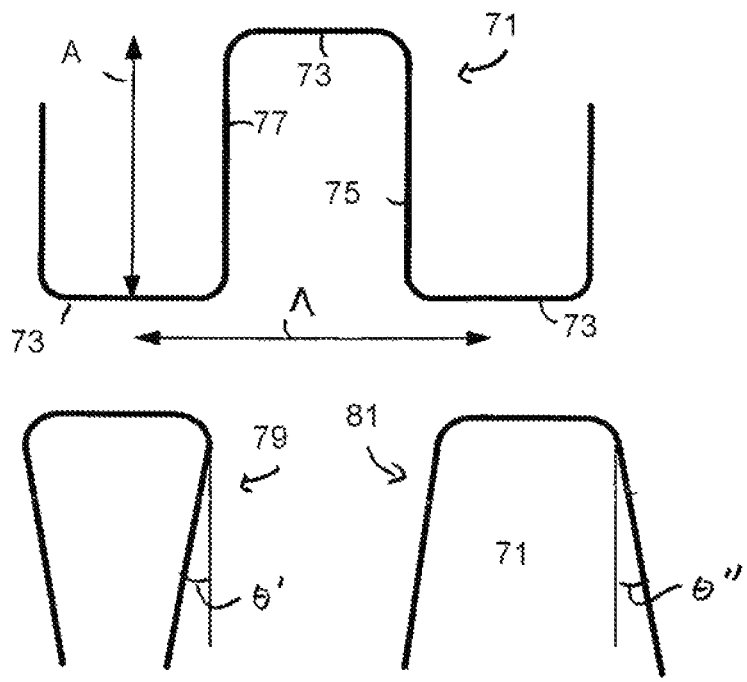
FIGS. 5A-B illustrate other embodiments of the preferred patterns of IP sensor conductors.

FIG. 5A is a stylized and exaggerated, but more quantitative, illustration how one embodiment of more square-like unit waves responds to stretch within an operational range. Pattern 71 represents an average operational level of stretch at which the unit wave has amplitude A and wavelength Λ. Since the largely linear bridging or cap portions 73 are generally more flexible than extensible, stretching an contracting is primarily accommodated by a moving apart or a moving together, respectively, of legs 75 and 77. Preferably, an average operational level of stretch, the sensor is designed so that at mid-range stretch the legs of the unit wave are substantially parallel as are legs 75 and 77. Then, when largely unstretched, the legs will slightly converge as pattern 79 (depicting an exaggerated convergence), while at maximum stretch, the legs will slightly diverge as pattern 81 illustrates (depicting an exaggerated convergence). It can be readily appreciated how such a design provides for pattern 71 with legs that are substantially parallel over most of the operational range of stretch.

In more detail, the legs of largely unstretched pattern 79 converge at approximately angle ΔΘ, and the legs of largely stretched pattern 81 diverge at approximate angle ΔΘ''. Preferably, ΔΘ' approximately equals ΔΘ'', and this angle ΔΘ is given approximately by the following relation (in degrees):

$$\Delta\Theta = \pm 28 * (\text{relative stretch } \Delta s/s \text{ in in/in})/(\text{frequency } F \text{ in/in}) * (\text{amplitude } A \text{ in in}).$$

Accordingly, where the relative stretch is 10% or less, the frequency is 5.5/in or greater and the amplitude is 0.35 in or greater, ΔΘ is approximately ±1.5°. Less preferably, pattern 71 represents a largely unstretched state and ΔΘ is then approximately −0°+3°, or pattern 71 represents a largely stretched state and ΔΘ is then approximately −3°+0° Note that the term "approximately parallel" is used with such a meaning, that is within approximately ±2° of being parallel across the operating range of stretch. The term "substantially parallel" is taken to mean parallel within manufacturing tolerances.

Therefore, generally preferably unit wave patterns have legs within approximately 3° of being parallel throughout an operating range of stretch. The term "substantially parallel throughout an operating range of stretch" is used with the meaning herein. It is more preferable to be deviate less from parallelism, e.g., approximately 1-2°, and less preferably to deviate more, e.g., approximately 4-5°. A variation of approximately 5° is an upper acceptable limit, while a deviation of approximately ±10° or greater is to be avoided.

Figure 5B:
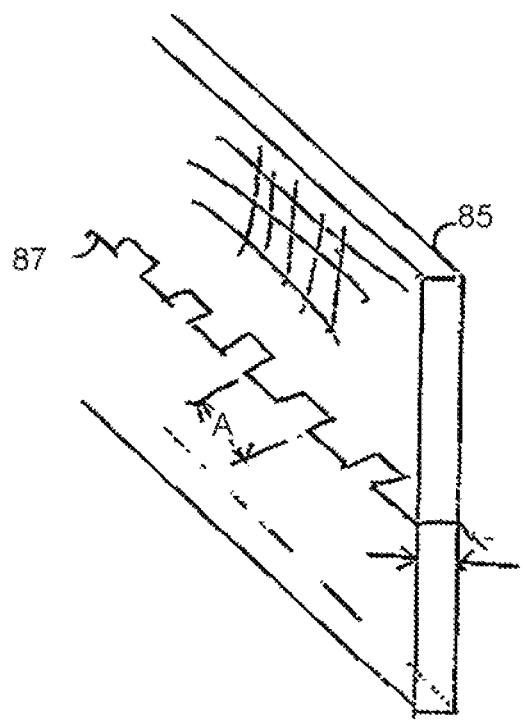

FIG. 5B schematically illustrates an alternative manner in which an IP conductor 87 can be attached to supporting elastic 85. Here, the conductor has unit waves that a transverse to the long axis of the elastic extending through the body of the elastic. It is preferred that in this attachment also the unit waves have the described preferred configuration. Here, square-like unit waves are illustrated having, an amplitude of A and a wavelength of Λ. The values of A and Λ are preferably scaled to achieve and amplitude-wavelength ratio of approximately ·2 of greater.

Wire (or other types of conductors) preferred for IP sensor conductor balances wire gauge (smaller diameter is mechanically more advantageous), resistance (lower is more advantageous), and physical flexibility (greater is more advantageous). Generally, wire with the finest possible gauge consistent with reasonable resistance is preferred. IT has been found that 27 or 29 AWG or higher wire with a resistance of 0.08 Ω/ft or less. Such wire is usually copper or silver coated copper within cost constraints. If insulated, insulation should have a low dielectric constant, such as expanded poly-tetrafluoro-ethylene. Preferred wire is also as flexible (also referred to herein as "limpness") as possible to permit proper stretch and relaxation. For example, an adequately limp wire will droop over the edge of an object under its own weight. Typically, high-strand wire, approximately 51/46 of better, has been found adequate.

Further aspects of IP sensor design include external connection. Both ends of an IP sensor conductor must be attached to sensor electronics, and such connection can be a point of failure since connections of all types, including joints, plugs and the like are known to fail more frequently than many other types of electrical components. This can be a particular problem for IP sensors because the elastic substrate, in contrast to metal or plastic bases, can easily tear. IP sensors are therefore preferably designed and constructed to have permanently attached external connections to the sensor conductor made at only one point along the sensor.

A preferred connection between sensor conductors and external wires has been found suitable in many sensor embodiments, especially those directed to ambulatory physiological monitoring. An external wire is soldered (low temperature solder) to the sensor conductor and a sleeve is crimped about the joint. This contact provides good electrical contact along with sufficient physical stability.

Further, to monitor many body parts, and especially for monitoring the thorax and abdomen, it is advantageous for an IP sensor and/or supporting garment to openable and closeable, e.g., along, a midline, of the sensor or garment, in order that a monitored wearer can easily don the sensor or garment. Such sensors and garments are illustrates in FIGS. 8, 9, and 10. A sensor or garment is usually provided with zippers, Velcro strips, clasps, or the like, so that it can be opened and closed, and these devices will necessarily interrupt the path of an IP sensor conductor crossing the midline. Such interruptions may require, in the absence of careful configuration, additional external contacts.

In a preferred configuration to minimize external contacts, sensor conductors are arranged in loops with a long longitudinal axis and an short transverse axis. The sensor conductors at one longitudinal end of the loop are bridged (or jumpered) together; the conductors at the other longitudinal loop end are available for external connection. The loop is then arranged around a monitored body part with the garment or sensor midline passing between opposite ends of the loop without problem. Preferred sensor conductor arrangements act as relative length sensors even when arranged in a loop having adjacent arms.

Figure 6A:
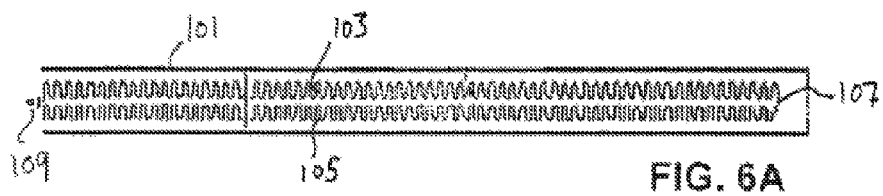
FIGS. 6A-C illustrate arrangement of IP sensor conductors in IP sensors.

FIG. 6A illustrates an exemplary such preferred configuration. IP sensor 101 having two IP conductors 103 and 105 configured with preferred unit waves. The two conductors are bridged at 107 to form a single loop. External connections to the free ends of the loop are limited to region 109. This sensor can then be arranged about a body part so that the sensor or garment midline, or closure axes, passes between the ends of the loop at 107 and 109. Since no external leads need cross the separation axis, this configuration requires no plugs for attachment and removal of any external bridging leads. FIGS. 6A-D are further described in the following.

Figure 6B:
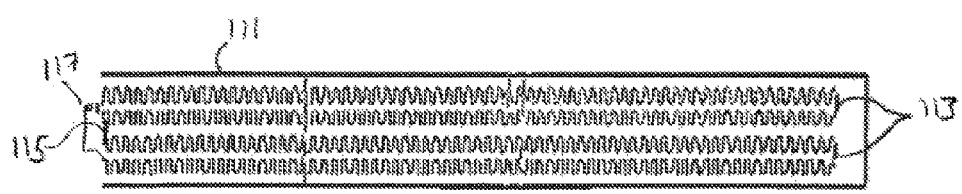
Figure 6C:
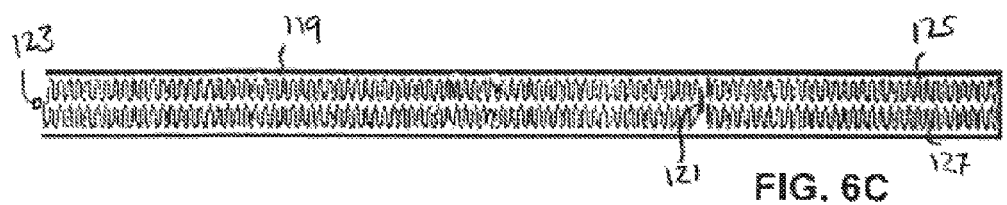

FIGS. 6B-C illustrate additional exemplary configuration in which sensor conductors are arranged in a loop in order to minimize external contacts. FIG. 6B illustrates IP sensor 111 having four IP conductors configured into a single folded loop. The two outer pairs of conductors are bridged 113 at one end, while the inner pair of conductors is bridged 115 at the opposite end. External connect ions are made to the two outer conductors at 117. Any even number of sensor conductors can be similarly configured. A functional alternative to four conductor sensor 111 is a two conductor sensor similar to 101 but having unit waves with twice the amplitude of the unit waves of sensor 111.

FIG. 6C illustrates is sensor 119 which is similar to sensor 111 but instead bridged at 121. External corrections are made at 123. Conductors 125 and 127 are externally unattached and not functional. This type of sensor is advantageous when it is needed to monitor only limited portion of a body part, i.e., the length between 121 and 123, without disturbing the remaining two lengths of conductors.

In some cases, an IP sensor, perhaps attached to or part of a garment, can be placed about a monitored body part by slipping the garment onto the part without need to opening or closing Here the a single sensor conductor can encircle the body part with external contacts made in a limited region. Bridging is not needed. Alternatively, one of the configurations illustrated in FIGS. 6A-D with bridged conductors can be used.

Multifunctional IP Sensors—Accessory Conductors

Figure 7A:
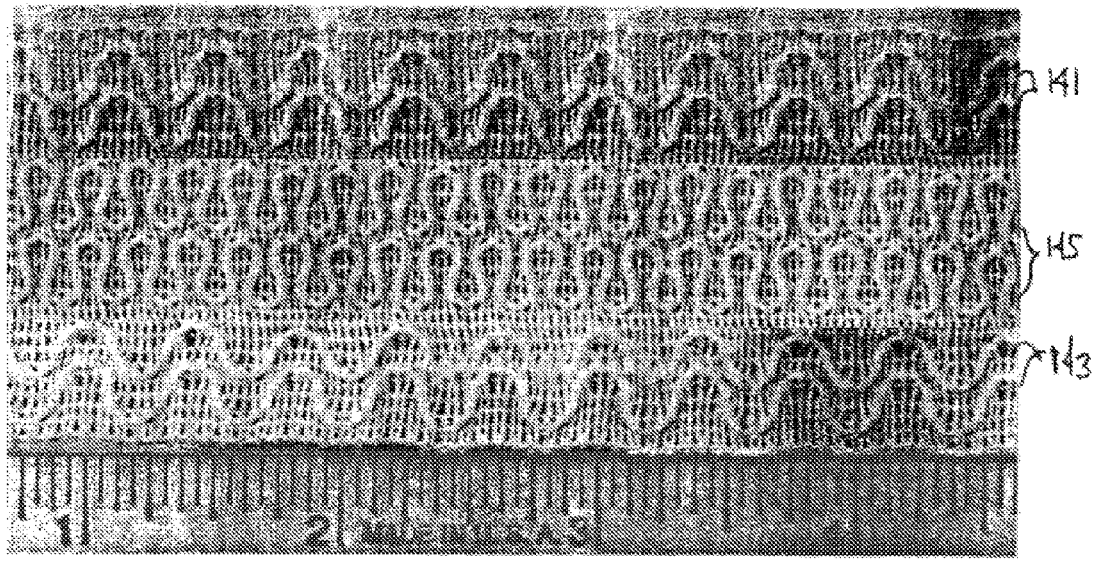
FIGS. 7A-B illustrate an implementation of the preferred patterns of accessory conductors.

In a further aspect of this invention, the supporting elastic of an IP sensor supports, in addition to the IP sensor conductors, additional conductive elements (referred to herein as "accessory conductors"), additional sensors, and the like, thereby forming a multifunctional IP sensor. Accessory conductors (also referred to herein as "channels") generally arranged in a linear fashion along a longitudinal dimension. FIG. 7A illustrates and IP sensor (similar but not identical to the IP sensors in FIGS. 4A-C) having two IP sensor conductors 145 along the midline of the supporting elastic, two accessory conductors 141 adjacent to the top edge of the supporting elastic, and two additional accessory conductors 143 adjacent to the bottom edge of the supporting elastic. The IP conductors and the accessory have different longitudinal wavelengths. Although their amplitudes here are approximately equal, in other embodiments their amplitudes can differ.

Types of linear conductive elements are suitable for this invention have sufficiently small size and sufficient flexibility to be incorporated into the supporting elastic, particularly elastic fabric, during its production process. Alternatively, accessory conductors (and IP sensor conductors) can be operably affixed to the supporting elastic in a post-production step. Conductive elements are incorporated or affixed to the supporting elastic in a manner so as not to impede the fabric's elasticity and/or stretch ability. Preferred conductive elements include bare or coated wire, shielded coated wire, coaxially shielded wire, and the like. Other types of possible conductive elements include flexible wires (with higher wire gauges) of virtually all types, including telephone-type wire and cables, twisted pairs, category 5 grade connections generally, ribbon wire, and the like.

IP sensor conductors are necessarily unshielded, typically of smaller wire sizes, and, as described, arranged at the preferred wavelengths and amplitudes and in the preferred patterns. Unshielded wire can also be used for interconnecting electronic components, for example, for interconnecting a sensor placed on or contiguous to the supporting elastic of an IP sensor with its elsewhere-located processing electronics. However, shielded wire or coax can be preferred to avoid electrical cross-talk and interference dues to adjacent IP sensors and other sources of electrical interference.

Preferred shielded wires, shielded wires, coax, and other conductive elements have an outside diameter (OD) of 1.0 mm or less, or 0.9 mm or less, or 0.8 mm or less, or 0.7 mm or less, or 0.6 mm or less, or 0.5 mm or less, and have a highly conductive element which is highly conductive, for example, having a resistance less than 0.1 ohm/foot. Copper is a preferred conductor; silver coated copper can be used if necessary. Preferred coats and insulations generally have low dielectric constant large breakdown voltage and include fluorinated ethylene polymers (FEP), silicone polymers, and the like. In particular, preferred wires include 29 gauge with high-count bare copper strands (51/46), with 0.083 ohm/foot, with 0.5 mm OD, and with FEP of silicone coating. Preferred coax has a 50 ohm impedance and a 0.81 mm OD. Small coax, also known as micro-coax, is available from, for example, Micro-Coax, Inc. (Pottstown, Pa.; http://www.micro-coax.com/(last visited Sep. 20, 2004)).

In order to accommodate the limited longitudinal elasticity of most conductive elements, preferred embodiments incorporate sufficient excess wire length so that, at the maximum stretch of the supporting elastic, the conductive elements will be under only minimal or no tension. Preferably, in an unstretched length S of supporting elastic a length of a conductive element W>S is incorporated or affixed that is equal to or greater than the maximally stretched length of the elastic, S'. Further, the conductive element is incorporated or affixed such as to permit the supporting elastic and the conductive element to move relatively during stretch. Thus, the conductive element will not be tensioned at any level of stretch throughout the maximal range of stretch. The length of conductive element per length of elastic is specified herein by the W−/−S ratio (greater than 1).

Conductive elements are incorporated or affixed to supporting elastic in a generally linear manner along the stretch axis but with repeated transverse (to the stretch axis) deviations so that W−S additional wire can be present into an elastic of length S. The transverse deviations are preferably in the plane of the elastic but can also be at an angle to this plane as in FIG. 5B, so that the conductive element extends both between the elastic surfaces. Although many forms of repeated, limited transverse deviations also possible, a preferred arrangement is in a prescribed pattern of limited curvature hi order to avoid kinks and breaks of the accessory conductors (excepting IP sensor conductors), especially of shielded wire, coax, and multi-wire cables.

Figure 7B:
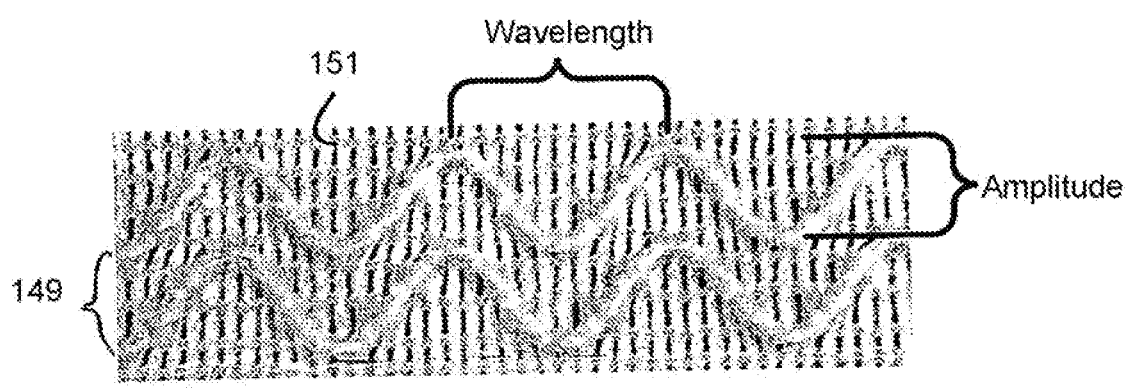

FIG. 7B illustrates a detail of two accessory conductors 149 affixed to a supporting elastic fabric 151. These conductors have a preferred pattern with a smoothly varying and limited curvature, here approximating a sinusoidal pattern. It can be appreciated how transverse deviations, determined by the wavelength, $\Lambda$, and amplitude, A, of the sinusoidal pattern, provide sufficient excess conductor length for elastic 151 to stretch without tensioning conductors 149. Conductors 149 are retained by the warp filaments in a manner permitting the sinusoidal pattern to readily flatten and lengthen, i.e., , increased $\Lambda$ and decreased A.

Preferably, the excess conductor length W−/−S

The W−/−S ratio is readily determined from the following relation:

$$W-/-S=(1.2/\Lambda)*SQRT(2*(A2)+\Lambda2)$$

For example, for an accessory conductor, if $\Lambda$=0.33 in. (frequency=3/in.) and A=0.22 in., then W−/−S=2.4. And for an IP sensor conductor, if $\Lambda$=0.2 in. (frequency=5/in.) and A=0.32 in., then W:F=3.8. Preferably, the excess conductor length, the W−/−S ratio, is adequate to prevent tensioning the conductor but not excessive in order to minimize weight, improve elasticity, and reduce cost (micro-coax currently being relatively expensive). A range of the W−/−S ratio from approximately 2 to approximately 3 has been found suitable.

In preferred multifunctional sensors, unshielded IP sensor conductors and accessory conductors each have each particular preferred characteristics, e.g., type of conductor, amplitude, and frequency. IP sensor conductors preferably have, as described above, an F (frequency 1/$\Lambda$) of approximately 5.0 or greater, to approximately 5.5 or greater, and approximately 6.0 or greater. Their amplitude, A, should usually be as large and an elastic can accommodate; one conductor with an A or approximately 0.6-1.0 in. or greater, or two conductors each with an A of approximately 0.30-0.40 inch or greater has been found suitable. Accordingly, IP conductors have larger W:F ratios Accessory conductors, e.g., shielded wire, or coax, or other types of wires, preferably have W:F ratios from approximately 2 to approximately 3. A and F can be chosen accordingly. For example, F can be approximately 2.5-3.5/in., and A can be approximately 0.3 inch to approximately 0.3 inch.

The supporting elastic should be wide enough to accommodate all conductors, or approximately the sum of the amplitudes of all supported conductors, within limits of subject comfort and acceptability. Multifunctional sensor can have from 1, to 2, to 4 or more IP sensor conductors with no accessory conductors or with 1, to 2, to 4, to 6, and to 8 or more.

Multifunctional IP Sensors—Additional Elements

IP sensors having accessory conductors can perform additional non-IP functions (referred to herein as "multifunctional IP sensors" or as "multifunctional sensors"). For example, the accessory conductors can electrically link additional sensors of various types to external connections and thereby to their processing devices. Preferably, additional sensor are adjacent to or in contact with the sensor or can be mounted on the supporting elastic of the sensor. A multifunctional IP sensor can have various physical arrangements configurations, e.g., from a band-like configuration extended along a single direction to configurations of approximately equal dimensions in all directions. Further, a multifunctional IP sensor can be configured as a garment to be worn by a monitored subject or can be mounted on supporting apparel. IP sensors can support 2, or 4, or 6, or more IP sensor conductors and 2, or 4, or 6, or more accessory conductors.

In the following, exemplary band-like multifunctional IP sensors having selected additional functions are illustrated and described. However, the described sensors are not limiting, and it be apparent to one of skill in the art from the following how multifunctional sensors of other configurations and functions can be constructed.

Figure 8A:
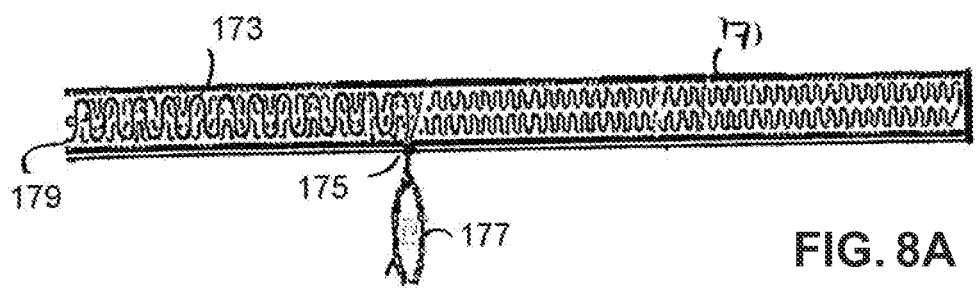
FIGS. 8A-C illustrate embodiments of multifunction IP sensors.
Figure 8B:
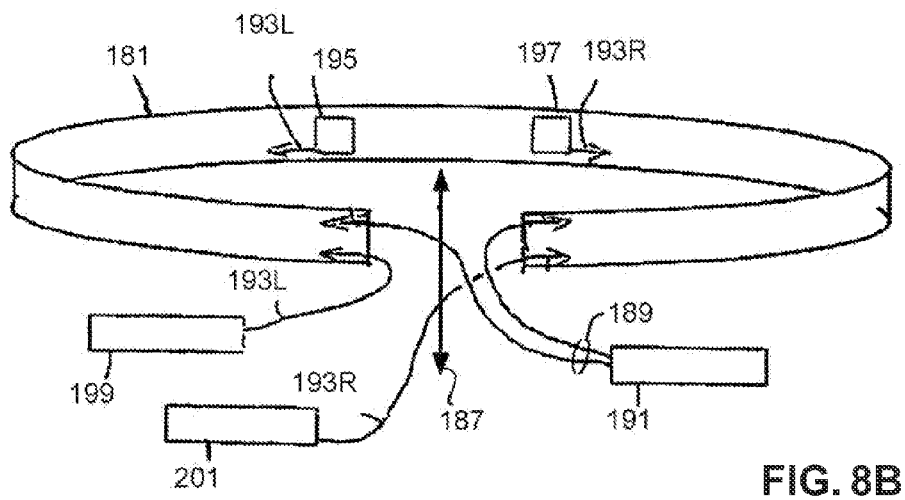
Figure 8C:
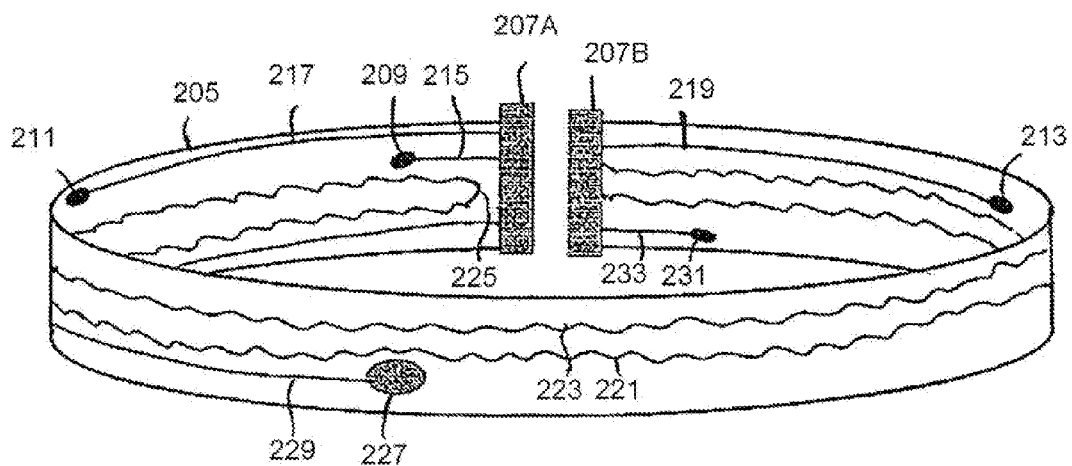

FIG. 8A-C schematically illustrate exemplary band-like multifunctional IP sensors. The sensors themselves can serve as apparel or be mounted on supporting apparel. For clarity, these figures do not provide details already described and illustrated. Importantly, both IP sensor conductors and accessory conductors are generally illustrated usually as simple lines without details. Actual implementations of these conductors will, however, have the characteristics already described. Also, details incidental to this invention are not shown. For example, snaps, buckles, electrical connectors, and the like, are illustrated only in outline as such elements can be supplied by one of skill in the art. Similarly, embodiments may require conductive elements for separate signal and ground connections, which also can be supplied by one of skill in the art and are not separately illustrated.

FIG. 8A illustrates simplified IP multifunctional sensor 171 having IP sensor conductors configured similarly to sensor 111 (FIG. 6A). Sensor 171 also supports accessory conductor 173 which connects externally through connector 175 to additional sensor 177, e.g., an antenna loop, which is placed adjacent to sensor 171. The accessory conductor also connects externally at connector 179, and electrically links the antenna to processing circuitry. The accessory conductor is illustrated as having a sinuous waveform with the above-described preferred characteristics.

FIG. 8B illustrates a IP multifunctional sensor 181 having two conductive elements and performing three sensor functions. Sensor 181 is for into a loop suitable for placing about, for example, the torso of an subject, and can be either incorporated as part of a, e.g., shirt-like or vest-like physiological monitoring garment perhaps including additional sensors, or it can be configured as a band-like garment with only such additional coverings as are necessary for comfort, convenience, and protection. The sensor can be provided with clasps, snaps, zippers, and the like, for their longitudinal connection across midline region 187. As illustrated, electrical connection to the sensor's conductive elements are made at left and right ends 183 of the sensor in midline region 187. In another embodiment, the sensor may be continuous and longitudinal connectors are can be dispensed with while electrical connection can be made to the conductive elements by the preferred connectors or other means at the sensor's outer face.

Conductive element 189 runs from one end of the sensor to the other end around the sensor without interruption and can server as an IP sensor. Although a loop configuration with external connection at only one end is generally preferred, the illustrated configuration is suitable especially when the sensor is continuous. Conductive element 189 is illustrated as linked to external IP sensor electronics 191.

Conductive elements 193L and 193R (collectively, 193) link to sensors 195 and 197. Left half 193L carries signals from sensor 195 to the left edge of the sensor, and right half 193R carries signals from sensor 197 to the right sensor edge. The portion between sensors 195 and 197 is electrically interrupted if necessary so that the signals from both sensor can be externally distinguished. Sensor electronics 199 processes, signals from sensor 195 and links to 193L. Similarly, sensor electronics 201 processes signals from sensor 197 and links to element 193R. Thereby, the single conductive element 193 (193L and 193R) can provide external connections for two separate sensors. In preferred embodiments, sensor electronics 191, 199 and 201 are packaged into a single physical module.

Sensors 195 and 197 can include various physiological sensors including, for example, microphones, thermometers, ECG electrodes, accelerometers, and the like, also sensors for electroencephalograms, electrooculograms, electromyograms, and the like, as well as other non-physiological sensors. They can be physically incorporated into or supported by the supporting elastic of sensor 181 or can be carried by associated apparel. Elements 195 and 197 can also be other components that can be sized and configured to be compatible with sensor 181, e.g., electronics modules perhaps for one or more of sensors 195, 197, and IP conductor 189.

FIG. 8C schematically illustrates another band-like multifunctional IP sensor 205 having six or more conductive elements and intended to encircling the thorax of a monitored subject. Although not illustrated in this figure for clarity, it should be understood that conductive elements extend entirely around the sensor but with electrical interruptions as necessary, and also have the preferred and previously-described patterns. In particular, IP sensor conductors have the preferred patterns described above (regardless of the illustration here).

Connectors 207a and 207b (collectively, 207) mechanically link both edges of the sensor and provide electrical connections between conductive elements on either side of the sensor and/or to external units. If the sensor is continuous, such connectors are not needed. Connections between conductive elements and external sensors can be made as known in the art by plugs, or by retainers holding the conductive element in contact with a conductive pad on the sensor, or by solder, or the like. Connections between conductive elements and sensors are preferably soldered joints covered by a sleeve as described.

In a preferred embodiment, sensor 205 includes an two IP sensor conductors 221 and 223 which are bridged into a single electrical loop at 225 and linked externally at single connector 207a. The sensor also supports three electrocardiogram (ECG) sensors 209, 211 and 213 on the sensor's inner side to be electrical contact with a subject's skin and distributed around the anterior thorax. These ECG electrodes are linked to connectors 207 (and on to external units) by shielded conductive elements 215, 217 and 219, respectively, to reduce electrical noise in the ECG signal.

Sensor 231, linked by shielded or unshielded conductive element 233, senses, in one embodiment, subject surface temperature. Sensor 227 linked by shielded conductive element 229 is, in one embodiment, an impact microphone sensitive to sounds of potentially dangerous impacts on the subject. Sensors 227 and 231; or additional sensors, can alternatively be accelerometers, and the like, or can also be electronic modules as described.

A Preferred Supporting Elastic Material

In preferred embodiments, the supporting elastic for the IP sensors and multifunctional IP sensors of this invention is formed into bands having longitudinal lengths that are considerably longer than their traverse width. For example, typical band widths (transverse sizes) are between 1 and 2 inches, or between 2 and 4 inches, or between 4 and 6 inches; and typical band lengths (longitudinal sizes) are from 1 foot to several hundred feet. Accordingly, this preferred supporting elastic is also referred to herein as "bands" or "elastic bands".

For an elastic band stretchable in the longitudinal direction, the filaments comprising the warp are elastomeric. Spandex® or Lycra® have proven most suitable in the present invention. These manmade strands have superior elasticity and have been found to be less abrasive and less irritating to bare skin than natural strands. However, for those applications in which direct contact between the skin and the fabric 10, 100 is not contemplated, extruded natural latex strands will provide satisfactory elasticity.

A variety of fill, or weft, yarns may be used to complete the formation of the supporting elastic material. While single ply, 150 denier polyester is quite suitable, other suitable yarns including 2 ply, 70 denier nylon; 2 ply, 100 denier nylon; and, 2 ply, 150 denier polyester, have been found suitable. However, other yarns, formed of natural and man-made materials, as well as other deniers, may also be suitably used. Further, bands preferably have selvage along longitudinal edges.

The elongated band of supporting elastic material can be formed in any of the conventional ways for forming elastic fabrics including warp knitting, weft knitting, weaving, or braiding. Warp knitting on a crochet machine is particularly suited to the present invention since this type of machine is easily adaptable to producing elastic fabric bands having narrow widths. One such machine is an 8-bar crochet machine manufactured by Jacob Muller as Model RD3-8/420 (8-bar, 420 mm).

Conductive elements can be operably affixed to the supporting elastic by sewing in a separate operation subsequent to formation of the band, but it has been found most efficient and cost effective to form the entire composite elastic and wire fabric integrally in the same knitting operation. When the conductive elements are affixed during elastic formation by knitting and the like, it has been found that a knitting pattern movement allowing the conductive element to remain between knitting needles for two consecutive stitches provides an optimal construction that permits the conductive elements to stretch uniformly as supporting elastic stretches.

In forming a knitted fabric structure, the crochet machine draws each individual warp yarn through a guide mounted on a guide bar. Tension is applied to stretch the warp yarns. Movements of a plurality of guide bars cause each yarn to loop around a needle. After the yarns are looped, the needle bar on the machine is moved so as to cause loops to be formed simultaneously at all needles, resulting in a whole knitted course. A yarn inlay is next drawn across the lower warp yarns. As the guide bar is displaced sideways by one or more needles, the upper and lower warp yarns change places before the next cycle produces another course. The displacing of the guide bar determines the structure of the fabric.

For an IP sensor with, e.g., three conductive wires having the same wavelengths, amplitudes, and unit waveforms, the machine is setup with the number of warp yarns (e.g., approximately 17 or more Lycra® warp yarns) and at least one nylon or polyester weft inlay yarn. Odd numbered warp yarns are on one beam or bar, while even numbered yarns are on another beam or bar. In addition to this, another beam or bar (referred to as the "control bar") of the three conductive wires is setup and fed through yarn guides that are directed by this control bar.

This control bar moves the three guides back and forth across the fabric in a repeating sequence positions (positions being defined by adjacent warp yarns) as the fabric is being formed, preferably remaining in each position of the sequence for approximately two stitches. This position sequence of the control bar determines the wavelength, amplitude, and unit waveform in which the conductive wires are affixed. Two or more conductive wires can be independently affixed with separate selected wavelengths, amplitudes, and unit waveforms (see, e.g., FIG. 7A) using a setup with two or more beams or bars that are separately controlled in separate repeating position sequences.

For example, for an IP sensor similar to that illustrated in FIG. 7A, the warp and weft filaments are woven in a conventional manner using up to four controlling bars. The control bars for the IP sensor conductors (145 in FIG. 7A) are programmed to have a position sequence of 0-0-0-4-4-4-0-0-0-4-4-4, and the control bars for the accessory conductors (141 and 143 in FIG. 7A) are programmed to have a position sequence of 0-0-1-1-2-2-3-3-2-2-1-1. An alternative position sequence for the accessory-conductor control bar is 0-0-1-1-2-2-3-3-4-4-3-3-2-2-1-1, which affixes an accessory conductor to an approximately 1.5 in. wide band with approximately 15 or more ware threads with a sinusoidal pattern having an amplitude and, wavelength of approximately 0.4 in. Alternatively, the elastic can be woven so that warp and weft filaments are at an approximately 45° angle to each other, to the conductors, and to the longitudinal edges of the elastic.

Other machine setup parameters can be routinely selected. In particular, the elastic is preferably formed under an tension approximate equal to the upper limit of the operational range of stretch. A stretch of approximately 80% has been found suitable for physiological monitoring embodiments. It is also preferable to put more tension on the warp filaments that retain the conductors.

In detail, setup instructions for an eight bar crocheting machine to make the IP sensor of FIG. 7A include the following:

| BAR | # (ends) | TYPE | SEQUENCE |
|---|---|---|---|
| 1 | 4 | 1/150 SD | 1 - 31 - 1 - 31 - 1 - 31 - 1 - 31 - 1 - 31 - 1 - 31 |
| 2 | 29 | 1120 clear | 1 - 2 - 2 - 1 - 2 - 1 - 2 - 1 - 2 - 1 - 2 |
| 3 | | | |
| 4 | 2 | Rip | 0 - 0 - 0 - 4 - 4 - 4 - 0 - 0 - 0 - 4 - 4 - 4 |
| 5 | 4 | Coaxial | 0 - 0 - 1 - 1 - 2 - 2 - 3 - 3 - 2 - 2 - 1 - 1 |
| 6 | 4 | 1/150 SD | 31 - 1 - 31 - 1 - 31 - 1 - 31 - 1 - 31 - 1 - 31 - 1 |
| 7 | | | |
| 8 | | | |
| Warps | 29 | 1/150 SD | |

The following instruction supplement the above table: needles—width—31-2; stretch at knitter—80+/−10%; stretch after 2 hours—80+/−10%; stretch after, calendar—n/c; front picks—18; back picks at knitter—30+/−1; back picks after 2 hours—30+/−1; back picks after calendar—n/c Those skilled in the art will appreciate that there are other ways to form constructions teat will function as desired. For example, an IP sensor can be formed by braiding in known manners. For another example, an IP sensor can be formed in a non-woven embodiment. At least one conductive wire, shaped in a sinusoidal arrangement is placed in a long narrow mold. Manufactured filaments; e.g., polyester, nylon, etc., are extruded and crisscrossed over at least one side of the shaped wire to form a web or mesh-like overlay. Finally, a film of elastomeric fiber is extruded to encapsulate one or both surfaces of the wire and web layers. When cooled and dried, this structure will stretch and contract to deliver a satisfactory, reliable output signal.

The inventive principles described herein can also be applied to produce this composite fabric in other shapes, such as sheets or tubes. For example, this present invention also includes embodiments in which two or more elongated supporting elastic bands are joined into a single supporting elastic band with multiple layers, or in which a single wider elastic band is folded longitudinally and joined to form a single elastic band with multiple layers. Two of more elastic bands each with a single wire type in a pattern preferred to that wire type can be joined into a multiple layer supporting elastic band. One band of a joined pair of elastic bands can have unshielded wires at 5-6/in. and the second elastic band can have coax at 2-3/in. Another multiple layer embodiment can circumvent conductive element-number limitations of elastic bands with useful widths. A single elastic band with a width of 3.5-4.5 inches can woven to accommodate up to 4-6 unshielded and up to 4-6 coax conductive elements, and then folded longitudinally one or more times and joined along free edges. A multifunctional IP sensor so constructed can have up to 8, or 10, or 12 conductive elements in a net width of approximately 1.75 to 2.25 includes Elastic band edges may be joined as is known in the art by stitching, by thermal bonding, by ultrasound bonding, and the like. Also two or more elastic bands or an elastic band folded one or more times can also simply enclosed in a thin fabric sleeve.

Regional Physiological Monitoring Apparel

IP sensors and multifunctional IP sensors of this invention can be arranged over portions or regions of a monitored subject so that movement of the underlying region are monitored (referred to herein as "regional physiological monitors" or "regional monitors"). As described, signals from IP sensor conductors are primarily responsive to the total length of the sensor. Therefore, signals from regional physiological monitors will be primarily sensitive to areas, circumferences, diameters, and similar measures depending on how they are arranged and the geometric constraints of their arrangement. For example, a regional sensor over an anterior portion of the thorax will sense expansion and contraction only of that underlying anterior portion, while a regional sensor encircling the thorax will sense expansion and contraction of the whole thorax.

Regional physiological monitors have many applications. For example, regional monitors over the left and/or right sides or the thorax and/or abdomen are most responsive to respiratory motions in the left and/or right lung, respectively, and provide indications of differential lung function. See, e.g., U.S. Pat. No. 5,159,935 issued Nov. 3, 1992 (which is incorporated herein by reference in its entirety for all purposes). Monitoring of differential lung function has numerous uses in assessing unilateral parenchymal disease, plural effusion or disease, pulmonary embolus, guarding due to pneumonia or other disease, and the like. Moreover, using such sensors, differential lung function can be monitored in ambulatory subjects.

Figure 9A:
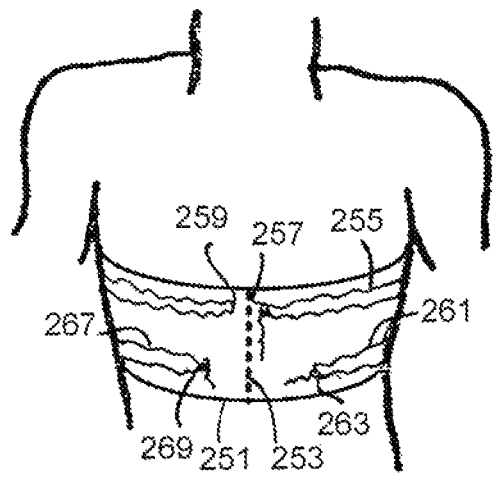
FIGS. 9A-C illustrate a garment including IP sensors.
Figure 9B:
Figure 9C:
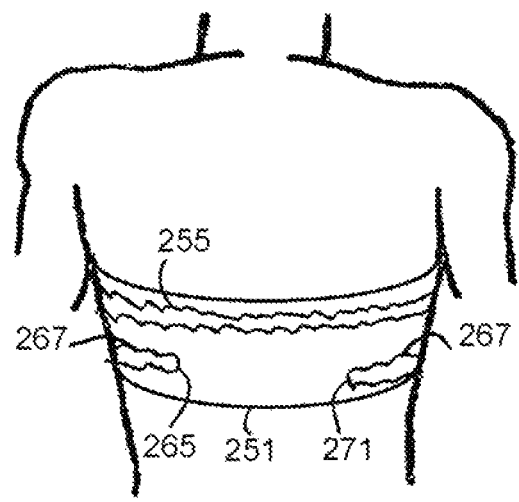

FIGS. 9A-C illustrate an exemplary embodiment of a regional physiological monitoring apparel. As in FIG. 8B-C, for clarity these figures, and subsequent FIG. 10A-B, do not provide details already described and illustrated. Importantly, both IP sensor conductors and accessory conductors are generally illustrated usually as simple lines without details. Actual implementations of these conductors will, however, have the characteristics already described.

Specifically, FIGS. 9A-C illustrate a garment including only IP sensor supporting elastic band 251 along with coverings useful for comfort and durability. FIG. 9A is an anterior illustration; FIG. 9B at lateral illustration; and FIG. 9C a posterior view. Identical reference numbers indicate the same structure on these three figures. This garment may be continuous for slipping over the head, or may have a zipper, Velcro strip, and the like along midline 253 so that it can be opened and closed. This garment and IP sensor includes three IP conductor loops, loops 255, 261, and 267.

Loop 255 largely encircles the rib cage and provides signals reflecting rib cage expansion and contraction, i.e., reflecting respiration. It includes two IP sensor conductors, bridge 259 between the conductors, and connectors 257 linking the conductors to external leads. Loop 261 overlays a left lateral portion of the rib cage and provides signals reflective of the expansion and contraction of the underlying regions of the left lung. This loop also includes two IP sensor conductors, bridge 265 between the conductors, and connectors 263 linking the conductors to external leads. Finally, loop 267 overlays a right lateral portion of the rib cage and provides signals reflective of the expansion and contraction of the underlying regions of the right lung. This loop also includes two IP sensor conductors, bridge 271 between the conductors, and connectors 269 linking the conductors to external leads. As described in U.S. Pat. No. 5,159,935, Signals from IP sensors 261 and 267 can be calibrated to yield indicia of left and right lung respiratory volumes, respectively, and the temporal variation of these respiratory volumes. See, e.g., U.S. Pat. No. 5,159,935.

Figure 10A:
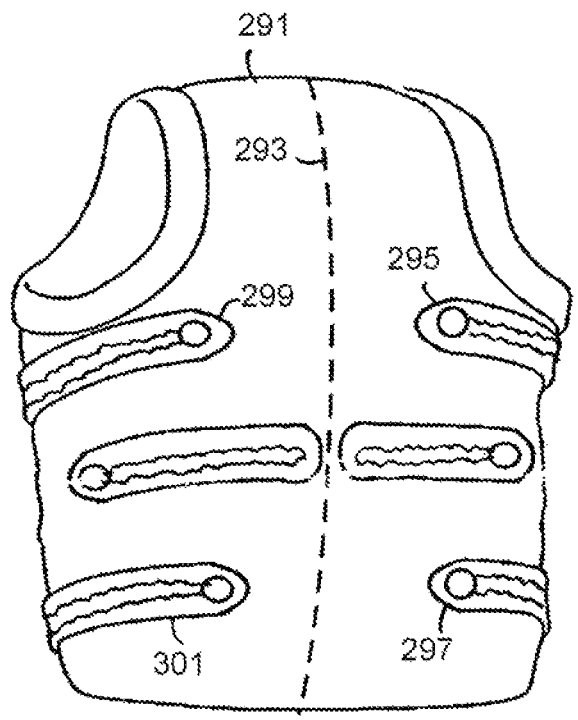
FIGS. 10A-B illustrate another garment including IP sensors.
Figure 10B:
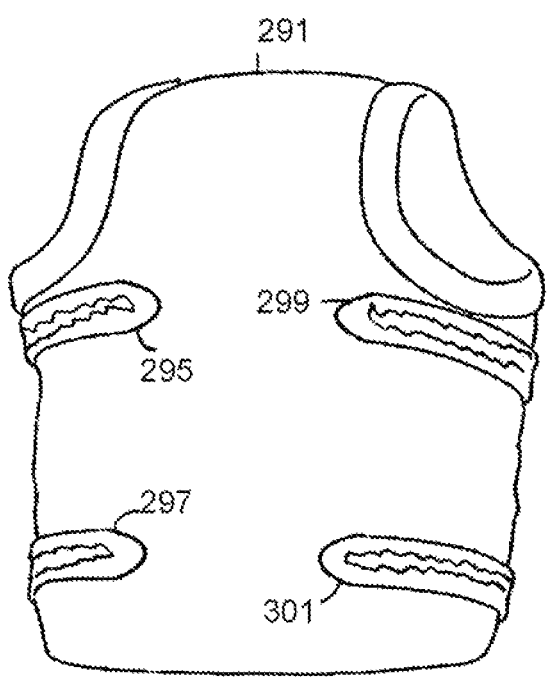

FIGS. 10A (anterior view) and 10B (posterior view) illustrate another exemplary embodiment of a regional physiological monitoring apparel. Garment 291 is in the form of a sleeveless shirt with midline closure 293, e.g., zipper, Velcro, or the like, for opening and closing the garment. If the garment is configured to be a pull-over, midline closure 293 can be dispensed with. The garment supports six IP sensors— 295, 297, 299, 301, 303 and 305—acting as regional monitors. Garment 291 is sufficiently elastic so that the expansions and contractions of underlying torso regions is reliably transmitted to the IP sensors. For simplicity, all the IP sensors are illustrated as including to sensor conductors which a bridged at one end to form an electrical loop. External contacts, schematically represented with the symbol "○" are provided and the other end of the conductors.

Comparing the signals from the supported IP sensors provides physiological monitoring information on total and right-left differences ("differential") lung and heart function. IP sensor 295 and 297 are primarily sensitive to regional expansions and contractions of the left portions of the rig cage and abdomen. As described, these signals can be combined into a reliable indication of left lung functioning. IP sensor 299 and 301 are primarily sensitive to regional expansions and contractions of the right portions of the rig cage and abdomen. As described, these signals can be combined into a reliable indication of right lung functioning. Differences between right and let lung function can indicate pathological conditions as described. The sum of the right and left lung function provides a reliable indication of overall respiratory function, including respiratory volumes and respiratory rates. Additionally, comparing signals from abdominal sensors 397 and 301 can indicate differential abdominal motions that can occur in abdominal disease, where it is know as "guarding", and other similar information.

IP sensors 305 and 303 are primarily sensitive to regional expansions and contractions of the left and right portions, respectively, of the anterior thorax. The sum of signals from both these sensors provides additional information on respiratory function and can include components reflective of cardiac pulsations. The difference of signals from these sensors provides additional information on differential respiratory function and can include components more reflective of cardiac pulsations, since these pulsations will primarily appear in signals from IP sensor 303 overlying the heart in comparison to signal from IP sensor 305.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A method for measuring physiological data of a user, comprising:
   providing two stretchable sensor conductors onto a body part of a user, wherein:
      each stretchable sensor conductor is configured to expand and contract with the movement of the body part,
      each stretchable sensor conductor includes an external contact point,
      the stretchable sensor conductors are connected through a bridging connection at a first end of the stretchable sensor conductors such that they form a single contiguous conductor at the first end of the stretchable sensor conductors, and
      the external contact points are located at a second end of the stretchable sensor conductors; and
   measuring an electrical characteristic of the stretchable sensor conductors which changes with expansion and contraction of the body part, to obtain physiological data.

2. The method of claim 1, wherein the stretchable sensor conductors operate in a frequency range of 150 kHz to 600 kHz.

3. The method of claim 1, wherein the stretchable sensor conductors operate in a frequency range of 300 kHz to 310 kHz.

4. The method of claim 1, further comprising:
   providing the stretchable sensor conductors around a rib cage of the user,
   wherein the electrical characteristic reflects rib cage expansion and contraction.

5. The method of claim 4, wherein the signals are calibrated to indicate the respiratory volume of the lungs.

6. The method of claim 1, wherein the stretchable sensor conductors are incorporated in a stretchable garment.

7. A method for measuring electronic physiological data of a user, comprising:
   providing two stretchable sensor conductors onto a body part of a user, wherein:
      each stretchable sensor conductor is configured to expand and contract with the movement of the body part,
      each stretchable sensor conductor includes an external contact point,
      the stretchable sensor conductors are connected through a bridging connection at a first end of the stretchable sensor conductors, and
      the external contact points are located at a second end of the stretchable sensor conductors;
   connecting the sensor conductors to an impedance measuring circuit;
   measuring an electrical characteristic of the stretchable sensor conductors which changes with expansion and contraction of the body part, to obtain electronic physiological data; and
   determining the impedance of signals received from the stretchable sensor conductors.

8. The method of claim 7, wherein the impedance measuring circuit includes an oscillator.

9. The method of claim 8, further comprising:
matching response characteristics of the stretchable sensor conductors with response characteristics of an oscillator circuit across the operating frequency range of the oscillator.

10. The method of claim 9, further comprising:
determining a frequency of an oscillator output signal; and
detecting the frequency of the oscillator output signal with a frequency detector.

* * * * *